United States Patent [19]

Baltz et al.

[11] Patent Number: 4,486,584
[45] Date of Patent: Dec. 4, 1984

[54] DEMETHYLMACROCIN COMPOUNDS AND DERIVATIVES THEREOF

[75] Inventors: Richard H. Baltz; Gene M. Wild, both of Indianapolis, Ind.; Eugene T. Seno, Norwich, England

[73] Assignee: Eli Lilly and Company, Indianapolis, Ind.

[21] Appl. No.: 450,879

[22] Filed: Dec. 20, 1982

Related U.S. Application Data

[62] Division of Ser. No. 169,051, Jul. 15, 1980, Pat. No. 4,385,116.

[51] Int. Cl.³ .................... C07H 17/08; C12P 19/62
[52] U.S. Cl. .................... 536/7.1; 424/180; 424/181
[58] Field of Search ........................ 536/7.1

[56] References Cited

U.S. PATENT DOCUMENTS

| | | | |
|---|---|---|---|
| 3,178,341 | 4/1965 | Hamill et al. | 435/896 X |
| 3,326,759 | 6/1967 | Hamill et al. | 435/896 X |
| 3,344,024 | 9/1967 | Whaley et al. | 435/898 X |
| 3,459,853 | 8/1969 | Gorman et al. | 424/121 |
| 4,056,616 | 11/1977 | Reimann et al. | 424/180 |
| 4,161,523 | 7/1979 | Weinstein et al. | 424/181 |
| 4,196,280 | 4/1980 | Umezawa et al. | 536/17 R |
| 4,201,843 | 5/1980 | Okamoto et al. | 435/76 |
| 4,205,163 | 5/1980 | Mori et al. | 536/17 R |
| 4,321,362 | 3/1982 | Baltz et al. | 536/7.1 |
| 4,357,325 | 11/1982 | Ose et al. | 536/7.1 |
| 4,373,095 | 2/1983 | Ganguly et al. | 536/7.1 |

FOREIGN PATENT DOCUMENTS 901273   7/1962   United Kingdom ............... 435/896

OTHER PUBLICATIONS

Omura et al., "Isolation and Characterization of a New 16-Membered Lactone, Protylonolide, from a Mutant of Tylosin-Producing Strain, Streptomyces fradiae KA-427", Chem. Pharm. Bull. 28 (6), 1963-1965 (1980).
Corcoran et al., "Relationship of Ribosomal Binding and Antibacterial Properties of Tylosin-Type Antibiotics," J. Antibiotics 30 (1), 1012-1014 (1977).
Tanabe Pharmaceutical, Japanese Examined Patent 6037-352 (Derwent Abstract 86253X/46 only).
S. M. Nash et al., Current Chemotherapy and Infectious Disease Proceedings of 11th ICC and the 19th ICAAC, American Society of Microbiology, pp. 462-463 (1980).
S. Masamune et al., J. Amer. Chem. Soc. 98 (24), 7874-7875 (1976).
T. Suzuki et al., Chemistry Letters 1973, 793-798.
A. Kinumaki et al., J. Antibiotics 30 (6), 450-454 (1977).
R. Okamoto et al., Japanese Kokai Tokkyo Koho 80 43,0183 [abstract from Chem. Abstr. 93: 68663u (1980) only].
Tanabe Pharmaceutical, Japanese Examined Patent 6037-351 (Derwent Abstract 86252X/46 only).
Seno et al., "Terminal Stages in the Biosynthesis of Tylosin", Chem. Abstr. 87: 71646 (1977).
H. Tsukiura et al., J. Antibiotics 22 (3), 89-99 (1969).
T. Yamaguchi et al., J. Antibiotics 31 (5), 433-440 (1978).
A. A. Nagel et al., J. Org. Chem. 44 (12), 2050-2052 (1979).

Primary Examiner—Johnnie R. Brown
Attorney, Agent, or Firm—Nancy J. Harrison; Arthur R. Whale

[57] ABSTRACT

2'''-O-demethylmacrocin (DOMM) which has the formula:

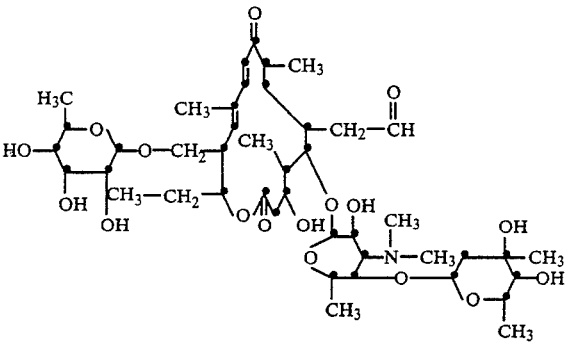

20-dihydro-DOMM, 2'''-O-demethyllactenocin (DOML), 20-dihydro-DOML, specified acyl ester derivatives, and their acid addition salts are useful antibacterial agents.

16 Claims, 1 Drawing Figure

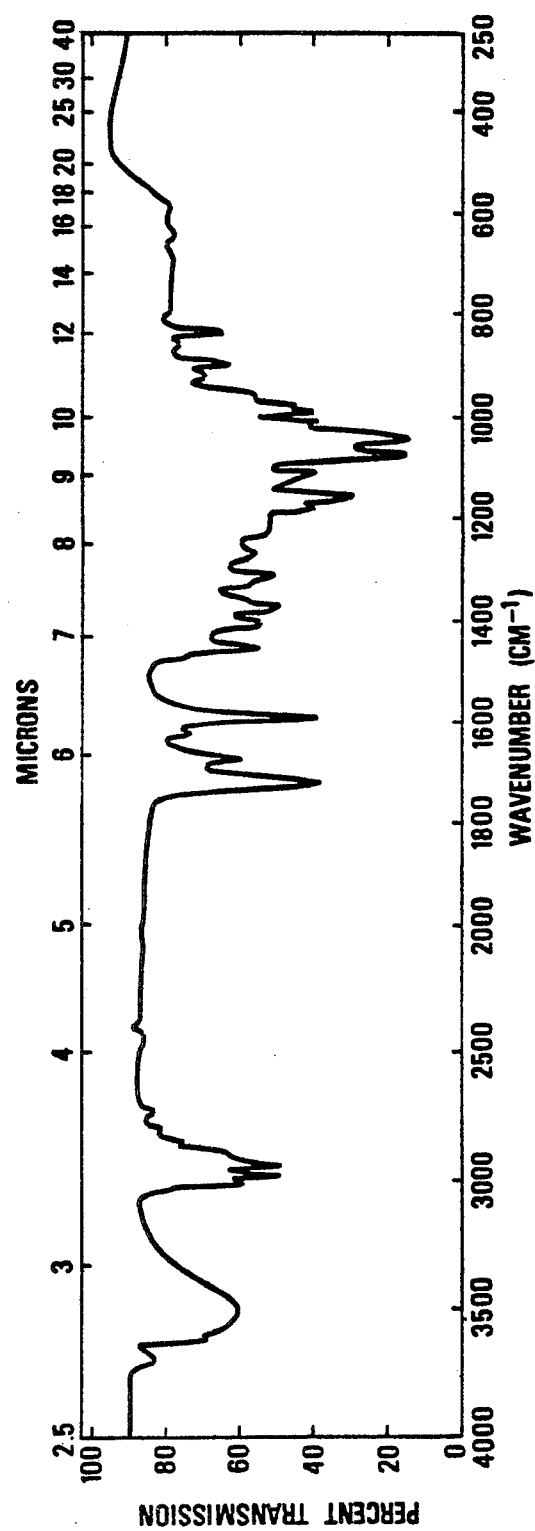

DEMETHYLMACROCIN COMPOUNDS AND DERIVATIVES THEREOF

This application is a division of application Ser. No. 169,051, filed July 15, 1980, U.S. Pat. No. 4,385,116.

SUMMARY OF THE INVENTION

This invention relates to 2'''-O-demethylmacrocin, a new macrolide antibiotic, and to its 20-dihydro derivative. 2'''-O-demethylmacrocin, which will be called demethylmacrocin or DOMM for convenience herein, has structure 1:

tral sugars in structure 1 are mycarose and 6-deoxy-D-allose, and the amino-sugar in 1 is mycaminose.

The dihydro-derivative of DOMM, i.e. 20-dihydro-2'''-O-demethylmacrocin, will be called dihydro-DOMM for convenience herein.

Dihydro-DOMM has structure 2:

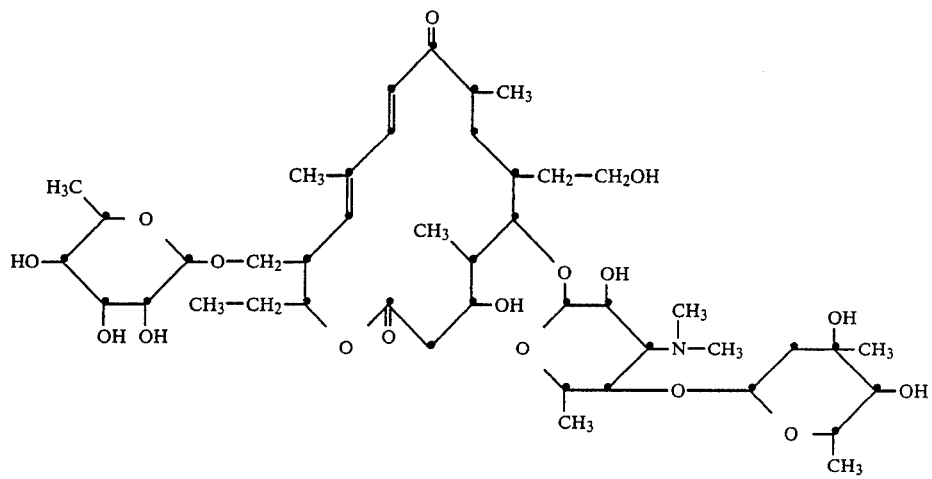

DOMM and dihydro-DOMM inhibit the growth of organisms which are pathogenic to animals. More specifically, DOMM and dihydro-DOMM are antibacterial agents which are especially active against grampositive microorganisms and Mycoplasma species.

This invention also relates to 2'''-O-demethyllactenocin (DOML) and 20-dihydro-2'''-O-demethyllactenocin (dihydro-DOML) and to methods of preparing DOML and dihydro-DOML by mild acid hydrolysis of DOMM and dihydro-DOMM, respectively.

DOML has structure 3:

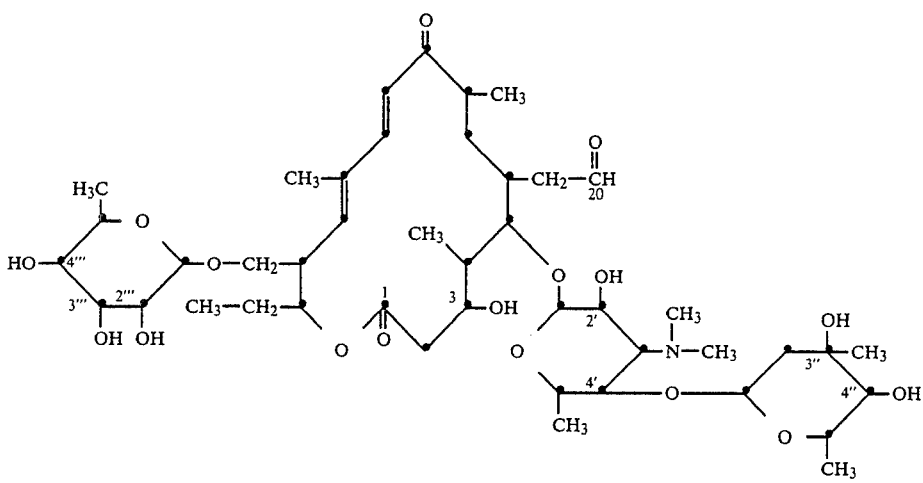

Although no stereochemical assignments are indicated in the structures given herein, the stereochemistry of the compounds is identical to that of tylosin. The neu-

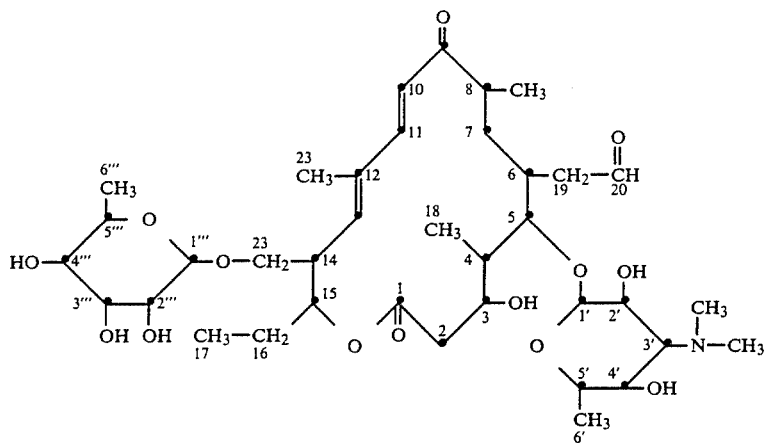

Dihydro-DOML has structure 4:

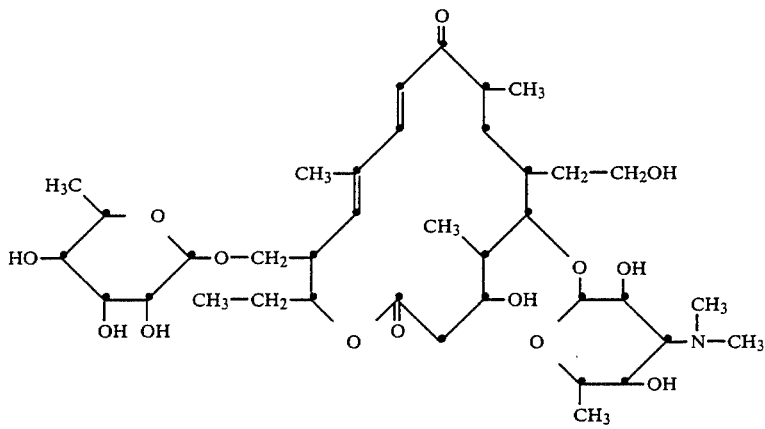

The hydroxyl groups of DOMM and dihydro-DOMM at the 2', 4", 3", 2"', 3"', 4"' and 3-positions can be esterified to form useful acyl ester derivatives. The hydroxyl groups of DOML and dihydro-DOML at the 2', 4', 2"', 3"', 4"' and 3-positions can be esterified to form useful acyl ester derivatives. In addition, dihydro-DOMM and dihydro-DOML can be esterified on the 20-hydroxyl group. Esterification of the 2'-hydroxyl group of DOMM and dihydro-DOMM is facile. The 2'- and 4'-hydroxyl groups of DOML and dihydro-DOML are readily esterified. Typical esters are those of a monocarboxylic acid or hemi-esters of a dicarboxylic acid having from 2 to 18 carbon atoms.

DOMM, dihydro-DOMM, DOML, dihydro-DOML, and their acyl ester derivatives are basic compounds which, when combined with acids, are converted to acid addition salts. These addition salts are also part of this invention. To simplify discussions of utility, the term "DOMM compound" is used and refers to DOMM, dihydro-DOMM, DOML, dihydro-DOML, a specified acyl ester derivative of these compounds, or a pharmaceutically acceptable acid addition salt of DOMM, dihydro-DOMM, DOML, dihydro-DOML or of their acyl ester derivatives.

This invention further relates to a new strain of *Streptomyces fradiae*, ATCC 31664, and to the method of producing DOMM or dihydro-DOMM by culturing this strain under submerged aerobic fermentation conditions until a substantial level of antibiotic activity is produced. DOMM or dihydro-DOMM can be extracted from basified broth filtrate with polar organic solvents, and can be further purified by extraction, adsorption and/or crystallization.

DESCRIPTION OF THE DRAWING

The infrared absorption spectrum of DOMM (free base) in chloroform is presented in the accompanying drawing.

DETAILED DESCRIPTION

DOMM

The following paragraphs describe the properties of DOMM. The structure of DOMM is shown in formula 1.

DOMM is a white solid which crystallizes from acetone-water. DOMM softens at about 135°–140° C. and melts completely by about 160° C. Elemental analysis of DOMM indicates that it has the following approximate percentage composition: carbon, 59.5%; hydrogen, 8%; nitrogen, 2%; oxygen, 30.5%. DOMM has an empirical formula of $C_{44}H_{73}NO_{17}$ and a molecular weight of about 888 (887 as determined by mass spectrometry).

The infrared absorption spectrum of DOMM (free base) in chloroform is shown in the accompanying drawing. Observable absorption maxima occur at the following frequencies ($cm^{-1}$): 3679 (small), 3604 (shoulder), 3486 (broad), 3012 (shoulder), 2979 (intense), 2938 (intense), 2880 (shoulder), 2821 (shoulder), 2794 (v. small), 2735 (v. small), 1723 (intense), 1678

(medium), 1627 (small), 1593 (intense), 1477 (shoulder), 1459 (medium), 1409 (medium), 1373 (medium), 1333 (shoulder), 1316 (medium), 1273 (small), 1183 (shoulder), 1161 (intense), 1114 (medium), 1080 (intense), 1048 (intense), 1013 (medium), 996 (medium), 984 (shoulder), 960 (shoulder), 924 (v. small), 902 (small), 865 (v. small), and 841 (small).

The ultraviolet absorption spectrum of DOMM in neutral ethanol exhibits an absorption maximum at 283 nm ($\epsilon$ 22,550).

DOMM (free base) has the following specific rotation: $[\alpha]_D^{25} -39.69°$ (c 1, $CH_3OH$).

Electrometric titration of DOMM in 66% aqueous dimethylformamide indicates the presence of a titratable group with a $pK_a$ value of about 7.14.

DOMM is soluble in water and in most polar organic solvents, such as acetone, methanol, ethanol, chloroform, dimethylformamide and dimethyl sulfoxide. DOMM acid addition salts are more soluble in water than is DOMM base.

DOMM can be distinguished from tylosin by paper and thin-layer chromatography. The approximate Rf and Rx values of DOMM and tylosin are summarized in Tables 1 and 2. In Table 2 Rx value is the ratio of movement expressed relative to that of tylosin, which was given a value of 1.0. Bioautography with *Bacillus subtilis* was used for detection.

TABLE 1

Thin-Layer Chromatography of DOMM[a]

| Compound | A[b] | B | C |
| --- | --- | --- | --- |
| Tylosin | 0.53 | 0.53 | 0.67 |
| DOMM | 0.05 | 0.44 | 0.44 |

[a]Medium: Merck, Darmstadt - Silica Gel 60
[b]Solvent:
A = ethyl acetate:diethylamine (96:4)
B = acetone:ethanol (2:1)
C = chloroform:methanol (3:1)

TABLE 2

Paper Chromatography of DOMM[a]

| Compound | D[b] | E |
| --- | --- | --- |
| Tylosin | 1.0 | 1.0 |
| DOMM | 0.17 | 0.88 |

[a]Paper: Whatman No. 1 treated with 0.75 M $KH_2PO_4$ buffer at pH 4.0 and dried
[b]Solvent:
D = ethyl acetate saturated with water
E = n-butanol saturated with water

Dihydro-DOMM

The dihydro derivative of DOMM can be obtained by chemical reduction or by fermentation. When preparing dihydro-DOMM by chemical reduction, known procedures such as, for example, treating DOMM with an approximately stoichiometric amount of sodium borohydride in an alcoholic solvent, may be used. Dihydro-DOMM is also produced by the *S. fradiae* ATCC of this invention under controlled fermentation conditions.

DOML and Dihydro-DOML

This invention also relates to DOML (the compound of formula (3) and to dihydro-DOML (the compound of formula (4). This invention further relates to methods of preparing DOML and dihydro-DOML by mild acid hydrolysis of DOMM and dihydro-DOMM, respectively. Dihydro-DOML can also be prepared by (1) mild acid hydrolysis of DOMM to give DOML followed by (2) reduction of DOML to give dihydro-DOML. Mild acid hydrolysis conditions are known in the art. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. At about pH 2 and at room temperature, the reaction time required is from about 6 to about 24 hours. The reaction is carried out by treating either DOMM or dihydro-DOMM with a mild acid solution for a time sufficient to effect removal of the mycarosyl group to give DOML or dihydro-DOML, respectively.

Alternatively, and sometimes preferably, DOML or dihydro-DOML can be prepared by treating DOMM or dihydro-DOMM in the fermentation broth in which it is produced, using mild acidic conditions as above described for a time sufficient to convert the DOMM or dihydro-DOMM to DOML or dihydro-DOML, respectively. DOML or dihydro-DOML thus prepared can be isolated from the fermentation broth using techniques known in the art.

Ester Derivatives

DOMM and dihydro-DOMM can be esterified at the 2', 4'', 3'', 2''', 3''', 4''' and 3-hydroxyl groups to give acyl ester derivatives by treatment with acylating agents using methods known in the art. DOML and dihydro-DOML can be esterified at the 2', 4', 2''', 3''', 4''' and 3-hydroxyl groups in a similar manner. In addition, dihydro-DOMM and dihydro-DOML can be esterified at the 20-position. Esterification of the 2'-hydroxyl group of DOMM and dihydro-DOMM is facile. The 2'- and 4'-hydroxyl groups of DOML and dihydro-DOML are readily esterified. Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide. Acylations can also be carried out enzymatically as described by Okamoto et al. in U.S. Pat. No. 4,092,473. Once formed, the acyl derivatives can be separated and purified by known techniques.

The 2'-monoester derivatives of DOMM and dihydro-DOMM can be prepared by selective esterification techniques generally known in the art, such as, for example, treatment of the antibiotic with a stoichiometric quantity (or a slight excess) of an acylating agent, such as an acyl anhydride, at from about 0° C. to about room temperature for from about 1 to about 24 hours until esterification is substantially complete. The 2'-monoester can be isolated from the reaction mixture by standard procedures such as extraction, chromatography and crystallization.

Useful esters are those of organic acids including aliphatic, cycloaliphatic, aryl, aralkyl, heterocyclic carboxylic, sulfonic and alkoxycarbonic acids of from 2 to 18 carbon atoms, and of inorganic acids, such as sulfuric and phosphoric acids.

Representative suitable esters include those derived from acids such as acetic, chloroacetic, propionic, butyric, isovaleric, alkoxycarbonic, stearic, cyclopropanecarboxylic, cyclohexanecarboxylic, β- cyclohexylpropionic, 1-adamantanecarboxylic, benzoic, phenylacetic, phenoxyacetic, mandelic and 2-thienylacetic acids, and alkyl-, aryl-, and aralkyl-sulfonic acids, the aryl- and aralkyl-acids optionally bearing substituents such as halogen, nitro, lower alkoxy and the like on the aromatic moiety. Suitable esters also include hemi-esters derived from dicarboxylic acids such as succinic, maleic, fumaric, malonic and phthalic acids.

Pharmaceutically acceptable ester derivatives are a preferred group. Other ester derivatives are useful, however, as intermediates.

Salts

DOMM, dihydro-DOMM, DOML, dihydro-DOML and their specified derivatives form acid addition salts. The acid addition salts of DOMM, dihydro-DOMM, DOML, dihydro-DOML and of their acyl derivatives are also part of this invention. Such salts are useful, for example, for separating, purifying and crystallizing DOMM, dihydro-DOMM, DOML, dihydro-DOML, and their acyl derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic and the like acids.

Pharmaceutically acceptable acid addition salts are an especially preferred group of salts of this invention. "Pharmaceutically acceptable" salts are salts in which the toxicity of the compounds as a whole toward warm-blooded animals is not increased relative to the non-salt form.

Preparation of OMT and Dihydro-OMT

This invention also provides additional methods of preparing 5-O-mycaminosyltylonolide (OMT) and 20-dihydro-5-O-mycaminosyltylonolide (dihydro-OMT). OMT and dihydro-OMT are described by Gorman et al. in U.S. Pat. No. 3,459,853. In U.S. Pat. No. 3,459,853, OMT and dihydro-OMT are prepared by removing the neutral sugars by controlled acid hydrolysis of tylosin, desmycosin, macrocin, and lactenocin and their dihydro-derivatives. This invention provides new starting materials from which OMT and dihydro-OMT can be prepared. Thus, using the method described in U.S. Pat. No. 3,459,853, DOMM and DOML can be used to prepare OMT; and dihydro-DOMM and dihydro-DOML can be used to prepare dihydro-OMT.

Preparation of DOMM and Dihydro-DOMM by S. fradiae

DOMM and dihydro-DOMM are prepared by culturing a strain of Streptomyces fradiae which produces these compounds under submerged aerobic conditions in a suitable culture medium until substantial antibiotic activity is produced. As will be appreciated by those skilled in the art, DOMM is produced first in the fermentation process. Dihydro-DOMM is produced when the fermentation is carried out for a longer time, thus permitting the DOMM present to be reduced enzymatically.

The culture medium used to grow Streptomyces fradiae ATCC 31664 can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal, and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of DOMM or dihydro-DOMM, submerged aerobic fermentation in tanks is preferred. Small quantities of DOMM or dihydro-DOMM may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

S. fradiae ATCC 31664 can be grown at temperatures between about 10° and about 40° C. Optimum antibiotic production appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Antibiotic production can be followed during the fermentation by testing samples of the broth against organisms known to be sensitive to these antibiotics. One useful assay organism is Staphylococcus aureus ATCC 9144. The bioassay is conveniently performed by an automated turbidometric method. In addition, antibiotic production can be readily monitored by ultraviolet (UV) absorption of the extracted broth. High-performance liquid chromatography with UV detection can also be used to monitor production [see, for example, J. H. Kennedy in J. Chromatographic Science, 16, 492-495 (1978)].

Following its production under submerged aerobic fermentation conditions, DOMM or dihydro-DOMM can be recovered from the fermentation medium by methods used in the fermentation art. Recovery of DOMM or dihydro-DOMM is accomplished by an initial filtration of the fermentation broth. The filtered broth can then be further purified to give the desired antibiotic. A variety of techniques may be used in this purification. A preferred technique for purification of the filtered broth involves adjusting the broth to about pH 9; extracting the broth with a suitable solvent such as ethyl acetate, amyl acetate, or methyl isobutyl ketone; extracting the organic phase with an aqueous acidic solution; and precipitating the antibiotic by making the aqueous extract basic. Further purification involves the use of extraction, adsorption and/or crystallization techniques.

The Microorganism

The new microorganism of this invention was obtained by chemical mutagenesis of a *Streptomyces fradiae* strain which produced tylosin. The microorganism obtained by mutagenesis produces only minimal amounts of tylosin, but produces DOMM as a major component.

For characterization purposes, the new organism was compared with *Streptomyces fradiae* strain M48-E 2724.1, a tylosin-producing strain derived from *S. fradiae* NRRL 2702. *S. fradiae* NRRL 2702 was disclosed by Hamill et al. in U.S. Pat. No. 3,178,341, issued Apr. 13, 1965. In the discussions herein the tylosin-producing *S. fradiae* M48-E 2724.1 culture will be called "E2724.1".

The new DOMM- and dihydro-DOMM-producing strain ATCC 31664 is also classified as a strain of *Streptomyces fradiae*. In characterizing this organism, the methods recommended for the International Streptomyces Project for the characterization of Streptomyces species have been followed [E. B. Shirling and D. Gottlieb, "Methods For Characterization of Streptomyces Species," *Internatl. Journal of Systematic Bacteriology*, 16 (3), 313–340 (1966)] along with certain supplementary tests. The following references to *S. fradiae* in the literature were consulted: (1) R. E. Buchanan and N. E. Gibbons, "Bergey's Manual of Determinative Bacteriology," 8th ed., The Williams and Wilkins Co., Baltimore, Md., 1974, p. 815; and (2) E. B. Shirling and D. Gottlieb, "Cooperative Description of Streptomyces. II. Species Description from First Study," *Internatl. Journal of Systematic Bacteriology*, 18 (2), 118, (1968).

The following description of the DOMM-producing strain compares its characteristics with those of the tylosin-producing *S. fradiae* strain "E2724.1".

Characterization Of The Microorganism

The spore-chain morphology of the new strain and of the E2724.1 strain is in the Retinaculum-Apertum (RA) section. Hooks, loops, and irregular coils are short and generally not of a wide diameter. This is best observed on ISP#2 (yeast-malt extract agar) for the E2724.1 strain and on calcium malate agar for the new strain. The spore surface is smooth; the spore shape is spherical with an average size of 0.65 $\mu$M in diameter. The diameter range is from 0.61 to 0.71 $\mu$M.

The most obvious differences between these strains are seen in their cultural characteristics. The E2724.1 strain produces aerial mycelia fairly well on most media and is in the White color series. The DOMM-producing strain produces very little, if any, aerial mycelia. When present, it is in the White to Gray color series. The reverse sides of these colonies have no distinctive pigments produced. They are light to moderate yellow in color. Melanoid pigment production is negative[1].

[1]Melanoid-pigment production was tested using ISP#1 (tryptone-yeast extract broth), ISP#6 (peptone yeast extract-iron agar), ISP#7 (tyrosine agar), and ISP#7 agar without tyrosine.

A summary of the important similarities and differences between the E2724.1 strain and the DOMM-producing strain is given in Table 3.

TABLE 3

| Comparison of *Streptomyces fradiae* E2724.1 and ATCC 31664 | |
|---|---|
| Similarities | Differences |
| Spore-chain morphology | Cultural characteristics |
| Spore-surface ornamentation | Carbon utilization |
| Spore size | Gelatin liquefaction |
| Lack of chromogenicity | NaCl tolerance |
| Lack of soluble pigments | pH range |
| Growth in selected vegetative media | Temperature range |
| Starch hydrolysis | |
| Negative skim milk reaction | |
| Nitrate reduction | |
| Catalase positive | |
| Phosphatase positive | |
| Urease negative | |
| Antibiotic sensitivity pattern | |

The morphology and growth characteristics of the *S. fradiae* E2724.1 and ATCC 31664 strains are compared in Table 4. In the tables which follow the antibiotic sensitivities (Table 5), carbon utilization (Table 6) and miscellaneous physiological characteristics (Table 7) are compared.

TABLE 4

| Growth Characteristics and Morphology | | | |
|---|---|---|---|
| | | E2724.1 | ATCC 31664 |
| Sporophores | | RA | RA |
| Spore chains | | >10 | >10 |
| Spore surface[1] | | smooth | smooth |
| Spore shape | | spherical | spherical |
| ISP#2 | G[2] | good | good |
| | R | 87. m. yellow[3] | 87. m. yellow |
| | Am | good 263. white | trace |
| | Sp | none | none |
| ISP#3 | G | poor | no growth |
| | R | 263. white | — |
| | Am | poor 263. white | — |
| | Sp | none | — |
| ISP#4 | G | abundant | good |
| | R | 87. m. yellow | 87. m. yellow |
| | Am | abundant 263. white | none |
| | Sp | none | none |
| ISP#5 | G | good | good |
| | R | 86.1. yellow | 86.1 yellow |
| | Am | good 92. y. white | none |
| | Sp | none | none |
| ISP#7 | G | abundant | good |
| | R | 87. m. yellow | 87. m. yellow |
| | Am | abundant 263. white | poor |
| | Sp | none | light brown |
| Bennett's | G | poor | no growth |
| | R | 90. gy. yellow | — |
| | Am | none | — |
| | Sp | none | — |
| Ca-malate | G | good | poor |
| | R | 263. white | 89. p. yellow |
| | Am | good 263. white | poor 263. white |
| | Sp | none | none |
| Czapek's | G | good | abundant |
| | R | 87. m. yellow | 87. m. yellow |
| | Am | abundant 263. white | none |
| | Sp | none | none |
| Glucose-asparagine | G | no growth | no growth |
| | R | — | — |
| | Am | — | — |
| | Sp | — | — |
| Tomato paste-oatmeal | G | abundant | good |
| | R | 92. y. white | 87. m. yellow |
| | Am | abundant 263. white | none |

TABLE 4-continued

Growth Characteristics and Morphology

|  | E2724.1 | ATCC 31664 |
|---|---|---|
| Sp | none | none |

[1]Spore-surface ornamentation was determined using a scanning electron microscope.
[2]G = Growth; R = Reverse or underside of colony; Am = Aerial mycelium; Sp = soluble pigment
[3]Color names were assigned using the ISCC-NBS color charts (K. L. Kelly and D. B. Judd, "The ISCC-NBS Centroid Color Charts Standard Sample No. 2106," U.S. Dept. of Commerce, National Bureau of Standards, Washington, D.C. 20234)

TABLE 5

Antibiotic Sensitivity[a,b]

| Antibiotic | Conc. | Class Compound | E2724.1 | ATCC 31664 |
|---|---|---|---|---|
| Chloramphenicol | 30 μg | nitrophenyl compound | + | + |
| Erythromycin | 15 μg | macrolide | tr | tr |
| Cephaloridine | 30 μg | β-lactam | + | + |
| Lincomycin | 2 μg | lincosaminide | — | — |
| Polymyxin B | 300 units | peptide | tr | + |
| Streptomycin | 10 μg | aminoglycoside | + | + |
| Tetracycline | 30 μg | tetracycline | + | + |
| Vancomycin | 30 μg | glycopeptide | + | + |

[a]Determined by using sensitivity discs padded onto seeded-agar plates.
[b]— = resistance (no zones of inhibition)
+ = sensitivity (zones of inhibition)
tr = trace of sensitivity

TABLE 6

Carbon Utilization[a,b]

| Carbon Source | E2724.1 | ATCC 31664 |
|---|---|---|
| Control: no carbon | — | — |
| Control: Glucose | + | + |
| L-Arabinose | — | + |
| D-Fructose | + | + |
| D-Galactose | + | + |
| i-Inositol | + | + |
| D-Mannitol | — | + |
| Raffinose | — | — |
| Salicin | — | — |
| Sucrose | + | + |
| D-Xylose | + | + |
| D-Rhamnose | — | + |

[a]— = no utilization
+ = utilization
[b]Determined on International Streptomyces Project (ISP)#9 (carbon-utilization agar) basal medium to which filter-sterilized carbon sources were added to equal a final concentration of 1.0%. Plates were incubated at 30° C. and observed after 7 and 12 days.

TABLE 7

Miscellaneous Physiological Characteristics

|  | E2724.1 | ATCC 31664 |
|---|---|---|
| ISP#1 (chromogenicity) | — | — |
| ISP#6 (chromogenicity) | — | — |
| ISP#7 (chromogenicity) | — | —[1] |
| Gelatin liquefaction | — | + |
| Skim-milk reaction | — | — |
| pH growth range[2,3] | 6.1–8.8 | 6.1–7.8 |
| Temperature growth range[2,4] | 10–37° C. | 10–30° C. |
| NaCl tolerance[2,5] | 8% | 6% |
| Starch hydrolysis[6] | + | + |
| Nitrate reduction | + | + |
| Catalase[7] | + | + |
| Phosphatase[7] | + | + |

TABLE 7-continued

Miscellaneous Physiological Characteristics

|  | E2724.1 | ATCC 31664 |
|---|---|---|
| Urease[7] | — | — |

[1]Small amount of light brown pigment observed at the top of the slant, but not distinct enough to be considered melanoid pigmentation
[2]On ISP#2 (yeast extract-malt extract agar) medium; incubated 7 days
[3]Determined using the following buffers at a concentration of 0.05 M: citric acid, pH 3, 4, 5; 2-(N—morpholino)ethanesulfonic acid, pH 6; 3-(N—morpholino)propanesulfonic acid, pH 7; N—2-hydroxyethylpiperazine-N'—2-ethanesulfonic acid, pH 8; 2-amino-2-(hydroxymethyl)-1,3-propanediol, pH 9; 3-cyclohexylamino-1,1-propanesulfonic acid, pH 10,11. The pH of the agar after seven days' incubation was taken as the correct value since some of the buffers failed to hold their adjusted pH. Buffer toxicity was tested by adjusting all the buffers to pH 7.0 and determining growth. No toxicity was noted.
[4]Tested at 5, 10, 15, 20, 25, 30, 37, 40, 45, 50 and 55° C.
[5]Measured by adding NaCl to the agar to equal: 0, 2, 4, 6, 8, 10 and 12% NaCl by weight
[6]Starch hydrolysis was determined by testing for the presence of starch with iodine on ISP#4 (inorganic salts-starch agar) plates
[7]The methods of Blazevic and Ederer were followed for the enzyme assays (D. J. Blazevic and G. M. Ederer, "Principles of Biochemical Tests in Diagnostic Microbiology," John Wiley and Sons, New York, N.Y., 1975).

Based on the foregoing characteristics the DOMM- and dihydro-DOMM-producing organism, ATCC 31664, is classified as a new strain of *Streptomyces fradiae*. This culture has been deposited and made part of the stock culture collection of The American Type Culture Collection, 12301 Parklawn Drive, Rockville, Md. 20852, from which it is available to the public under the accession number ATCC 31664.

As is the case with other organisms, the characteristics of *Streptomyces fradiae* ATCC 31664 are subject to variation. For example, recombinants, variants or mutants of the ATCC 31664 strain may be obtained by treatment with various known physical and chemical mutagens, such as ultraviolet rays, X-rays, gamma rays, and N-methyl-N'-nitro-N-nitrosoguanidine. All natural and induced variants, mutants and recombinants of *Streptomyces fradiae* ATCC 31664 which retain the characteristic of production of DOMM may be used in this invention.

Activity of DOMM Compounds

The DOMM compounds inhibit the growth of pathogenic bacteria, especially gram-positive bacteria and Mycoplasma species. Table 8 summarizes the minimal inhibitory concentrations (MIC), as measured by standard agar-dilution assays, at which DOMM (free base) inhibits certain bacteria.

TABLE 8

In Vitro Activity of DOMM Free Base

| Organism | MIC (μg/ml) |
|---|---|
| *Streptococcus pyogenes* C203 | 0.25 |
| *Streptococcus pneumoniae* Park I | 0.25 |
| Streptococcus sp. (Group D) 282 | 4.0 |
| *Pasteurella multocida* | 12.5 |
| *Pasteurella hemolytica* | 50.0 |
| *Mycoplasma gallisepticum* | 0.78 |
| *Mycoplasma hyopneumoniae* | 0.78 |
| *Mycoplasma hyorhinis* | 3.12 |

The DOMM compounds have shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. The $ED_{50}$ values observed for DOMM are given in Table 9.

TABLE 9

| Subcutaneous ED$_{50}$ Values (mg/kg × 2) of DOMM | | |
|---|---|---|
| Streptococcus pyogenes C203[a] | Streptococcus pneumoniae Park I[b] | Staphylococcus aureus 3055[c] |
| 1.1 | 37.5 | 3.8 |

[a]Bacterial challenge (X LD$_{50}$) = 133
[b]Bacterial challenge (X LD$_{50}$) = 41.2
[c]Bacterial challenge (X LD$_{50}$) = 139

In order to illustrate more fully the operation of this invention, the following examples are provided:

EXAMPLE 1

A. Shake-flask Fermentation of DOMM

A lyophilized pellet of *Streptomyces fradiae* ATCC 31664 is dispersed in 1-2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* ATCC 31664 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DOMM

In order to provide a larger volume of inoculum, 60 ml of incubated vegetative medium, prepared in a manner similar to that described in section A, is used to inoculate 40 liters of a second-stage vegetative growth medium having the following composition:

| Ingredient | Amount (%) |
|---|---|
| Corn steep liquor | 1.0 |
| Soybean meal | 0.5 |
| Yeast extract | 0.5 |
| CaCO$_3$ | 0.3 |
| Soybean oil (crude) | 0.5 |
| Lecithin (crude) | 0.015 |

-continued

| Ingredient | Amount (%) |
|---|---|
| Water | 97.185 |

Adjust pH to 8.5 with 50% NaOH solution.

This second-stage vegetative medium is incubated in a 68-liter tank for about 40 hours at 29° C., with adequate aeration and agitation.

Incubated second-stage medium (4 L) is used to inoculate 44 liters of sterile production medium having the following composition:

| Ingredient | Amount (%) |
|---|---|
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |

Adjust pH to 7.2 with 50% NaOH solution.

The inoculated production medium is allowed to ferment in a 68-liter tank for about four days at a temperature of 28° C. The fermentation medium is aerated with sterile air to keep the dissolved oxygen level between about 30% and 50% and is stirred with conventional agitators at about 250 rpm.

EXAMPLE 2

Isolation of DOMM

Fermentation broth (38 L), obtained as described in Example 1, is filtered with the use of a filter aid. The mycelial cake is washed with water; this water wash is added to the filtrate.

The pH of the filtrate is adjusted to 9.1, using a 25% aqueous solution of sodium hydroxide. The filtrate is extracted twice with ethyl acetate (9 and 5 L). Deionized water (3500 ml) is added to the ethyl acetate extract. The pH of this solution is adjusted to about pH 4.1, using a 28% phosphoric acid solution (2 parts water to one part concentrated phosphoric acid). After extraction, the aqueous phase is separated. The ethyl acetate extract is extracted again with water (3500 ml) using this procedure. The two aqueous extracts are combined.

The combined aqueous extracts are adjusted to pH 8.5 with sodium hydroxide and are extracted twice with chloroform (3000- and 1200-ml portions). The chloroform extracts are dried under vacuum to give about 40 g of crude DOMM base. This is purified by crystallization from water-acetone to give about 30 g of DOMM base.

EXAMPLE 3

Preparation of DOML

DOMM, prepared as described in Example 2, is dissolved in a dilute hydrochloric acid solution (HCl added to water until the pH of the solution is 1.8). The resulting solution is allowed to stand for about eight hours at room temperatures and then is adjusted to pH 9.0 by the addition of sodium hydroxide. This basic solution is extracted with ethyl acetate, dichloromethane or chloroform. The extract is dried under vacuum to give DOML base (softens at 115°–120° C. and melts at about 134°–140° C.).

EXAMPLE 4

Preparation of Dihydro-DOMM

DOMM (50 mg), prepared as described in Example 2, is dissolved in an aqueous isopropyl alcohol solution (approximately 40%; 25 ml). Sodium borohydride (20 mg) is dissolved in a 30% aqueous isopropyl alcohol solution (10 ml). The NaBH$_4$ solution (1 ml) is added to the solution containing the DOMM. The resulting mixture is stirred for 5 minutes, is adjusted to pH 7.5 with phosphoric acid, and is concentrated under vacuum to remove the isopropyl alcohol. Water is added to the resulting aqueous concentrate to give a volume of 25 ml; chloroform (50 ml) is added. The pH of the aqueous phase is adjusted to 7.5. After extraction, the chloroform is separated and evaporated to dryness under vacuum to give dihydro-DOMM.

EXAMPLE 5

Preparation of Dihydro-DOML

Dihydro-DOMM, prepared as described in Example 4, is treated in the manner described in Example 3 to give dihydro-DOML.

EXAMPLE 6

Alternative Preparation of DOML

DOML is prepared from DOMM by treating the DOMM in the fermentation broth in which it is produced with mild acid as described in Example 3. Isolation of DOML is accomplished by a procedure similar to that described for DOMM in Example 2.

EXAMPLE 7

Alternative Preparation of Dihydro-DOML

DOML, obtained as described in Example 3, is reduced using the procedure described in Example 4 to give dihydro-DOML.

EXAMPLE 8

2'-O-Propionyl-DOMM

DOMM is dissolved in acetone and treated with 1.2 equivalents of propionic anhydride at room temperature for about six hours to give 2'-O-propionyl-DOMM.

EXAMPLES 9–11

2'-O-Isovaleryl-DOMM, prepared according to the procedure of Example 8, but using isovaleric anhydride.

2'-O-Benzoyl-DOMM, prepared according to the procedure of Example 8 but using benzoic anhydride.

2'-O-(n-Butyryl)DOMM, prepared according to the procedure of Example 8, but using n-butyric anhydride.

EXAMPLE 12

2',4'-Di-O-Propionyl-DOML

DOML is dissolved in acetone and treated with slightly more than two equivalents of propionic anhydride at room temperature for about six hours to give 2',4'-di-O-propionyl-DOML.

EXAMPLES 13–15

2',4'-Di-O-isovaleryl-DOML, prepared according to the method of Example 12, but using isovaleric anhydride.

2',4'-Di-O-benzoyl-DOML, prepared according to the method of Example 12, but using benzoic anhydride.

2',4'-Di-O-(n-butyryl)DOML, prepared according to the method of Example 12, but using n-butyric anhydride.

We claim:

1. A compound selected from the group consisting of (1) 2'''-O-demethylmacrocin; (2) 20-dihydro-2'''-O-demethylmacrocin; (3) 2'''-O-demethyllactenocin; (4) 20-dihydro-2'''-O-demethyllactenocin; (5) the 2'-monoesters of 2'''-O-demethylmacrocin and of 20-dihydro-2'''-O-demethylmacrocin; (6) the 2',4'-diesters of 2'''-O-demethyllactenocin and 20-dihydro-2'''-O-demethyllactenocin, wherein each of said esters is an ester of a monocarboxylic acid or a hemi-ester of a dicarboxylic acid, each of 2 to 18 carbon atoms; and (7) the acid addition salts of (1) through (6).

2. The compound of claim 1 which is 2'''-O-demethylmacrocin.

3. The salts of claim 1 which are pharmaceutically acceptable.

4. The salt of claim 3 which is 2'''-O-demethylmacrocin tartrate.

5. The salt of claim 3 which is 2'''-O-demethylmacrocin hydrochloride.

6. The salt of claim 3 which is 2'''-O-demethylmacrocin phosphate.

7. The compound of claim 1 which is 20-dihydro-2'''-O-demethylmacrocin.

8. The compound of claim 1 which is 2'''-O-demethyllactenocin.

9. The salt of claim 1 which is 2'''-O-demethyllacetenocin tartrate.

10. The salt of claim 1 which is 2'''-O-demethyllactenocin phosphate.

11. The compound of claim 1 which is 2'-O-propionyl-2'''-O-demethylmacrocin.

12. The compound of claim 1 which is 2'-O-propionyl-2'''-O-demethylmacrocin tartrate.

13. The compound of claim 1 which is 2'-O-propionyl-2'''-O-demethylmacrocin phosphate.

14. The compound of claim 1 which is 2',4'-di-O-propionyl-2'''-O-demethyllactenocin.

15. The compound of claim 1 which is 2',4'-di-O-propionyl-2'''-O-demethyllactenocin tartrate.

16. The compound of claim 1 which is 2',4'-di-O-benzoyl-2'''-O-demethyllactenocin.

* * * * *